United States Patent [19]

Harrison

[11] Patent Number: 5,880,123
[45] Date of Patent: Mar. 9, 1999

[54] HEMOLYSIS PREVENTION BY NON-IONIC SURFACTANTS

[75] Inventor: Timothy Harrison, Great Dunmow, United Kingdom

[73] Assignee: Merck Sharp & Dohme Limited, Hoddesdon, England

[21] Appl. No.: 860,399

[22] PCT Filed: Dec. 15, 1995

[86] PCT No.: PCT/GB95/02936

§ 371 Date: Jun. 20, 1997

§ 102(e) Date: Jun. 20, 1997

[87] PCT Pub. No.: WO96/19970

PCT Pub. Date: Jul. 4, 1996

[30] Foreign Application Priority Data

Dec. 23, 1995 [GB] United Kingdom .................. 9426104

[51] Int. Cl.$^6$ .................................................. A61K 31/535
[52] U.S. Cl. ...................... 514/236.2; 514/922; 514/937; 514/943
[58] Field of Search ................... 514/236.2, 922, 514/937, 943

[56] References Cited

FOREIGN PATENT DOCUMENTS

A 27 30 570  1/1978  Germany .
WO 95/18124  7/1995  WIPO .

OTHER PUBLICATIONS

CA 116:11227, Kaneki et al., May 1991.

Friess, et al., *Pharmazie,* vol. 49, No. 2–3, pp. 197–201 (Feb.–Mar., 1994).

Sajadi Tabassi, et al., *J. Pharm. Pharmacol.,* vol. 46, No. Suppl., 4 p. 1060 (1994, Dec.).

Biesendorfer, et al., *Biochemical Pharmacology,* vol. 30, No. 16, pp. 2287–2292 (Aug. 1981).

Bock, et al., *Congr. Int. Technol. Pharm.,* 6th, vol. 4, pp. 380–387 (1992).

Hagerstrand, et al., *Biochimica Biophysica Acta,* vol. 1109, pp. 117–126 (1992).

*Primary Examiner*—Kimberly Jordan
*Attorney, Agent, or Firm*—J. Eric Thies; David L. Rose

[57] ABSTRACT

The present invention relates to the use of a non-ionic surface-active agent or an emulsion for the reduction of the hemolytic effects of an amphiphilic compound. There is also provided a method for reducing the hemolytic effects of an amphiphilic compound which comprises formulating said compound with a non-ionic surface-active agent or in the form of an emulsion.

4 Claims, No Drawings

HEMOLYSIS PREVENTION BY NON-IONIC SURFACTANTS

This application is a 371 of PCT/GB95/02936, filed Dec. 15, 1995.

This invention relates to the novel use of a non-ionic surface-active agent (otherwise known as a surfactant or wetting agent) or an emulsion for the reduction of the hemolytic effects of an amphiphilic compound.

Hemolysis of red blood cells (erythrocytes) is observed when such cells are suspended in a solution which has a lower osmotic pressure than that of the fluid in the red blood cells—i.e. when the solution is hypotonic. This has the effect of causing the red blood cells to swell and burst due to diffusion of water into the cells. Conversely, if red blood cells are suspended in a hypertonic solution—i.e. where the osmotic pressure is greater than that of the fluid in the cells—they may lose water and shrink (crenation).

This classical view of hemolysis has resulted in the development of "isotonic solutions" which exert the same osmotic pressure as blood plasma. In isotonic solution (e.g. 0.9% sodium chloride) red blood cells maintain their "tone" and the solution is said to be isotonic with human erythrocytes.

Hemolysis following parenteral administration of a pharmaceutical formulation may cause localised tissue damage, irritation, anaemia and in extreme cases may lead to organ damage, particularly damage to the kidneys.

It is now apparent, however, that hemolysis is not only caused by the administration of a hypotonic parenteral formulation. It has been observed that amphiphilic compounds will also exhibit hemolytic effects on red blood cells, even when administered in an isotonic solution.

Surprisingly, it has now been found that a non-ionic surface-active agent or emulsion can be used to dramatically reduce the hemolytic effects of an amphiphilic compound.

There is therefore provided in a first aspect of the present invention, the use of a non-ionic surface-active agent or an emulsion for the reduction of the hemolytic effects of an amphiphilic compound.

In an alternative aspect of the present invention, there is provided a method for reducing the hemolytic effects of an amphiphilic compound which comprises formulating said compound with a non-ionic surface-active agent or in the form of an emulsion.

Surface-active agents, otherwise known as surfactants or wetting agents are generally molecules which comprise a hydrophobic portion (e.g. an alkyl chain) and a hydrophilic portion (e.g. a polar or ionic group).

Surface-active agents may be divided into a number of classes including anionic agents, cationic agents, amphoteric agents and non-ionic agents, of which the non-ionic agents are particularly useful in the present invention.

Non-ionic agents include fatty alcohols; glyceryl esters such as the naturally occurring mono-, di- and triglycerides; fatty acid esters of fatty, and other, alcohols such as propylene glycol, polyethylene glycol, sorbitan, sucrose and cholesterol; polyoxyethylene sorbitan fatty acid esters; and polyoxyethylene ethers.

Particularly preferred non-ionic surface-active agents are the polyoxyethylene sorbitan fatty acid esters which are commercially available under the trade-name Tween™, for example, the monooleate ester (Tween 80™).

The precise choice of non-ionic surface-active agent and the concentration used will depend largely upon the physical properties of the chosen agent. It is believed that the masking of the hemolytic nature of an amphiphilic compound in accordance with the present invention is effected by the formation of micelles by the surface-active agent. Micelle formation occurs over a range of concentration of the surface-active agent known as the critical micellization concentration (cmc). It is therefore desirable to use in the present invention a concentration of the non-ionic surface-active agent which falls within the cmc range for the chosen agent. Micelles are formed by surface-active agents due to the lack of affinity of the hydrophobic regions of the surfactant molecules for their aqueous environment. An aggregate is therefore formed by strong hydrophobic chain-chain interactions in the "core" of the micelle, presenting the hydrophilic (polar) region of the molecules on the surface of the micelle. The lipophilic or non-polar region of the hemolytic amphiphilic compound is believed to be held in the hydrophobic centre of the micelle thus preventing its damaging interaction with erythrocyte cell membranes immediately upon injection.

Compositions with a non-ionic surface-active agent will conveniently comprise between 0.05 and 5% surface-active agent and preferably between 0.1 and 2.5%.

Formulation as an emulsion may be effected by mixing the amphiphilic compound with a commercially available fat emulsion, such as Intralipid™, Liposyn™, Infonutrol™, Lipofundin™, and Lipiphysan™. The compound may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with an emulsifier such as a phospholipid (e.g. egg phospholipids, soybean phospholipids, or soybean lecithin) and water.

The administration of an amphiphilic compound in an emulsion is believed to mask hemolysis in a similar fashion to that described for surface-active agent micelles, above. The hemolytic amphiphilic compound is believed to be dissolved in fat droplets which are suspended in an aqueous medium in the form of an emulsion. The amphiphilic compound is therefore prevented from interacting with erythrocyte cell membranes immediately upon injection.

Suitable emulsions will typically contain up to 20% oil, for example, between 5 and 20%. The fat emulsion will preferably comprise fat droplets between 0.1 and 1.0 $\mu$m, particularly 0.1 and 0.5 $\mu$m.

Particularly preferred emulsion compositions are those prepared by mixing the amphiphilic compound with Intralipid™ or the components thereof (soybean oil, egg phospholipid, glycerol and water).

It will be appreciated that other ingredients may be added to the formulation. Thus, for instance, bulking substances or tonicity modifiers may be added such as glycerin, lactose, mannitol, dextrose, sodium or potassium chloride, sodium sulphate and sorbitol, in general at a concentration up to 5% depending upon the chosen substance.

Other additives include antimicrobial preservatives, including benzalkonium chloride, benzethonium chloride, benzyl alcohol, chlorobutanol, chlorocresol, cresol, methyl p-hydroxybenzoate, phenol, phenylethyl alcohol, phenylmercuric nitrate and acetate, propyl p-hydroxybenzoate, and thimerosal; antioxidants, including acetone sodium bisulphite, ascorbic acid, ascorbic acid esters, butylhydroanisol, butylhydroxytoluene, cysteine, nordihydroguaiaretic acid, sodium bisulphite, sodium formaldehyde sulphoxylate, sodium metabisulphite, and tocopherols; and buffers, including acetic acid and a salt, citric acid and a salt, glutamic acid, and phosphoric acid salts.

As used herein, the term "amphiphilic compound" means a molecule which comprises both a hydrophilic (e.g. polar)

region and a hydrophobic (e.g. non-polar) region. The hydrophobic region of the molecule will exhibit a greater lipid solubility than the hydrophilic region hence erythrocyte membranes may be disrupted by such amphiphilic compounds.

The hydrophilic region of a molecule will typically be characterised by a polar or ionic group such as an amino moiety, for example, a teriary amino group such as dimethylamino. Such groups may be affected by local pH. The hydrophobic region may be, for example, an alkyl chain or a part of the molecule bearing one or more aryl moieties such as phenyl groups.

It will be appreciated that there are countless amphiphilic compounds which rely upon their physical properties in order to reach their intended site of action. For instance, drug molecules which act centrally on the central nervous system (CNS) must be able to cross the blood-brain barrier in order to penetrate the brain. This may be facilitated by their lipophilic nature. These properties only become a problem when the amphiphilic compound is administered by injection and the concentration of the compound in the blood immediately surrounding the needle-tip is high and therefore hemolysis is more likely to occur. Hemolysis can, in such instances, be avoided by slow infusion of the drug substance or by increasing the dose volume if possible, however, these procedures may be inconvenient or impractical and place an extra burden upon the attendant clinical physicians.

Hemolysis may be measured by the following method in vivo:

Male Sprague-Dawley rats (280 to 450 g) are anaesthetised with isoflurane. The tail artery and tail vein are cannulated with polythene tubing (0.58 mm internal diameter, 0.96 mm external diameter) and a small amount of heparinized saline (0.2 to 0.5 ml) is washed in (heparin concentration 10 units/ml). The rats are placed in restrainers and left to recover for 30 minutes to 1 hour. A baseline blood sample is taken 10 minutes before dosing with the test compound. The rats are then dosed with the test compound at t=0 minutes. Typically, 1–10 ml/kg of a 1–10 mg/ml solution is injected through the tail vein catheter over a period of 2 minutes and washed in with heparinized saline.

After dosing, small blood samples (approximately 400 μl) are taken at intervals over 1 hour (typically t=5, 10, 15, 30 and 60 minutes) from the tail artery catheter ensuring that the catheter is cleared to get fresh blood which is uncontaminated by the previous sample. Blood withdrawn is replaced with equal volumes of physiological saline. Blood samples are transferred directly into heparinized tubes (typically Microtainers™) and put on ice.

The assay for hemolysis is effected by centrifuging the blood samples to obtain a plasma fraction. The plasma is then decanted into plastic tubes and scored by eye for hemolysis (calorimetric cuvettes may be used for measurement of free haemoglobin using a spectrophotometer). Samples of plasma may be frozen at −18° C. or below if needed for later analyses.

Hemolysis is scored by the following system:

−=no difference
±=borderline: very slight pink colouration
+=mild: slight pink colouration
++=moderate: pink-red colouration
+++=marked: red colouration
++++=severe: very dark red colouration The following table shows the scores obtained using the compound 2-(R)-(1-(R)-bis(trifluoromethyl)phenyl)ethoxy) 4-(5-(N,N-dimethylaminomethyl)-1,2,3-triazol4-yl)methyl- 3-(S)-phenylmorpholine (Compound A), and the effect of performing the assay using Compound A in varying concentrations of Tween 80™ (polyoxyethylene sorbitan monooleate) or Compound A in Intralipid™ (soybean oil, egg phospholipid, glycerol and water). 5% Mannitol is included in each vehicle to adjust the tonicity.

TABLE

| test composition (in 5% mannitol) | solution conc. (mg/ml) | dose volume (ml/kg) | dose (mg/kg) | hemolysis score |
|---|---|---|---|---|
| Compound A | 1 | 10 | 10 | +++ |
| Compound A in 1.0% Tween 80 ™ | 2 | 10 | 20 | +/− |
| Compound A in 1.5% Tween 80 ™ | 2.5 | 10 | 25 | − |
| Compound A in 2.0% Tween 80 ™ | 5 | 5 | 25 | ++ |
| Compound A in 10% Intralipid ™ | 2 | 10 | 20 | − |
| Compound A in 10% Intralipid ™ | 4 | 5 | 20 | − |
| Compound A in 10% Intralipid ™ | 10 | 2 | 20 | ++ |

From the above results it is clear that Compound A, which exhibits marked hemolysis in the above in vivo assay when administered alone in 5% mannitol, is not hemolytic when formulated with a non-ionicsurface active agent (with Tween 80™) or in an emulsion (with Intralipid™). As shown by the above results, moderate hemolysis is only observed when the solution concentration (i.e. the concentration of Compound A at the needle tip on injection) is elevated (at 5 mg/ml with Tween 80™ and at 10 mg/ml with Intralipid™).

The following Examples illustrate pharmaceutical compositions which may be used in accordance with the present invention.

EXAMPLE 1—(Surface-Active Agent) Injection Formulation

| Active Ingredient(s) | up to 10 mg/kg |
|---|---|
| Tween 80 ™ | up to 2.5% |
| [in 5% aqueous mannitol (isotonic)] | |

The active ingredient(s) is (are) dissolved directly in a solution of the commercially available Tween 80™ (polyoxyethylenesorbitan monooleate) and 5% aqueous mannitol (isotonic).

EXAMPLE 2—(Emulsion) Injection Formulation

| Active Ingredient(s) | up to 30 mg/ml |
|---|---|
| Intralipid ™ (10–20%) | |

The active ingredient(s) is (are) dissolved directly in the commercially available Intralipid™ (10 or 20%) to form an emulsion.

EXAMPLE 3—Alternative (Emulsion) Injectable Formulation

|  | Amount |
| --- | --- |
| Active Ingredient(s) | 0.1–10 mg |
| Soybean oil | 100 mg |
| Egg Phospholipid | 6 mg |
| Glycerol | 22 mg |
| Water for injection | to 1 ml |

All materials are sterilized and pyrogen free. The active ingredient(s) is (are) dissolved in soybean oil. An emulsion is then formed by mixing this solution with the egg phospholipid, glycerol and water. The emulsion is then sealed in sterile vials.

I claim:

1. A method for reducing the hemolytic effects of an amphiphilic compound which comprises formulating said compound with a non-ionic surface-active agent.

2. The method as claimed in claim 1 wherein the non-ionic agent is selected from the group consisting of fatty alcohols; glyceryl esters; fatty acid esters of fatty, and other, alcohols; polyoxyethylene sorbitan fatty acid esters; and polyoxyethylene ethers.

3. The method as claimed in claim 2 wherein the non-ionic surface-active agent is a polyoxyethylene sorbitan fatty acid ester.

4. The method as claimed in claim 1 wherein the formulation comprises between 0.05 and 5% surface-active agent.

* * * * *